United States Patent
Miyauchi

(10) Patent No.: US 7,202,047 B2
(45) Date of Patent: Apr. 10, 2007

(54) AQUEOUS METHOD FOR DETERMINING CHOLESTEROL IN REMNANT-LIKE PARTICLES USING CHOLESTEROL ESTERASE, PHOSPHOLIPASE, SURFACTANT AND CHOLESTEROL OXIDASE OR DEHYDROGENASE

(75) Inventor: Kazuhito Miyauchi, Tagata-gun (JP)

(73) Assignee: Kyowa Medex Co., Ltd., Tokyo (JP)

( * ) Notice: Subject to any disclaimer, the term of this patent is extended or adjusted under 35 U.S.C. 154(b) by 355 days.

(21) Appl. No.: 10/430,231

(22) Filed: May 6, 2003

(65) Prior Publication Data

US 2003/0207342 A1 Nov. 6, 2003

Related U.S. Application Data

(63) Continuation of application No. 09/788,393, filed on Feb. 21, 2001, now abandoned.

(30) Foreign Application Priority Data

Feb. 28, 2000 (JP) .............................. 2000-050902

(51) Int. Cl.
*C12Q 1/60* (2006.01)
(52) U.S. Cl. ........................................................ 435/11
(58) Field of Classification Search .................. 435/11, 435/19; 436/71
See application file for complete search history.

(56) References Cited

U.S. PATENT DOCUMENTS

| 5,041,636 | A |   | 8/1991  | Sakata et al.        |
|-----------|---|---|---------|----------------------|
| 5,164,512 | A |   | 11/1992 | Hashizume et al.     |
| 5,238,818 | A |   | 8/1993  | Hashizume et al.     |
| 5,635,468 | A |   | 6/1997  | Ara et al.           |
| 6,114,134 | A | * | 9/2000  | Kishi et al. ........ 435/11 |
| 6,794,157 | B1 | * | 9/2004 | Sugiuchi ............. 435/11 |
| 6,986,998 | B2 | * | 1/2006 | Kishi et al. ........ 435/11 |

FOREIGN PATENT DOCUMENTS

| DE | 3319066   | 11/1984 |
| EP | 0 698 791 | 2/1996  |
| EP | 0 699 767 | 3/1996  |
| EP | 0 763 741 | 3/1997  |
| EP | 0 764 848 | 3/1997  |
| EP | 1 020 532 | 7/2000  |
| GB | 1 555 173 | 11/1979 |
| JP | 8-105875  | 4/1996  |
| JP | 8-105876  | 4/1996  |

OTHER PUBLICATIONS

Tanaka A. Postprandial Hyperlipidemia and Remnant Lipoprotein. Arteriosclerosis 25(9, 10)371-6, 1998, translation provided.*
Nakajima K. et al. A New Approach for the Detection of Type III Hyperlipoproteinemia by RLP Cholesterol Assay, J of Atherosclerosis and Thrombosis 1(1)30-36, 1994.*
Uematsu, et al., "Relation between micellar structure of model bile and activity of esterase", Biochmica et Biophysica Acta, vol. 1258, No. 2 (1995), pp. 122-134.

* cited by examiner

*Primary Examiner*—Ralph Gitomer
(74) *Attorney, Agent, or Firm*—Fitzpatrick, Cella, Harper & Scinto

(57) ABSTRACT

The present invention provides a simple and sensitive aqueous method for determining cholesterol in remnant-like particles in a biological sample without the separation of components of the sample. The method comprises contacting the sample with (i) cholesterol esterase, (ii) cholesterol oxidase or cholesterol dehydrogenase, and (iii) phospholipase with a surfactant that inhibits cholesterol oxidase or cholesterol dehydrogenase in lipoproteins other than remnant-like particles in the presence of oxygen or an oxidized coenzyme. Formed hydrogen peroxide or reduced coenzyme is measured and correlated to a quantitative determination of cholesterol in remnant-like particles.

12 Claims, 1 Drawing Sheet

AQUEOUS METHOD FOR DETERMINING CHOLESTEROL IN REMNANT-LIKE PARTICLES USING CHOLESTEROL ESTERASE, PHOSPHOLIPASE, SURFACTANT AND CHOLESTEROL OXIDASE OR DEHYDROGENASE

This application is a continuation of application 09/788,393 filed Feb. 21, 2001, now abandoned, which claims priority to Japan application 050902/00 filed Feb. 28, 2000.

BACKGROUND OF THE INVENTION

The present invention relates to a method and a reagent for the quantitative determination of cholesterol in remnant-like particles which is considered as a risk factor for arteriosclerosis and other diseases in clinical tests.

In clinical tests, cholesterol in high density lipoprotein (HDL) is considered as a negative risk factor for arteriosclerosis and cholesterol in low density lipoprotein (LDL) is considered as a positive risk factor for arteriosclerosis. Thus, the determination of cholesterol of such classes is frequently performed in the field of clinical testing. In recent years, it has been demonstrated that cholesterol in lipoproteins formed by lipid metabolism and the like is a more closely linked risk factor for arteriosclerosis than LDL cholesterol. Such lipoproteins include remnant-like particles, and the determination of cholesterol in remnant-like particles is given health insurance scores by the Ministry of Health, Labour and Welfare in Japan.

For the determination of cholesterol in remnant-like particles, a method is known which comprises separating remnant-like particles from a sample using anti apolipoprotein B100 antibody and anti apolipoprotein A1 antibody, and measuring cholesterol in the separated remnant-like particles [Arteriosclerosis (Domyakukoka), 25 (9, 10), 371 (1998)]. However, this method employs affinity chromatography using antibodies and requires separation of components of a sample, which makes it a cumbersome and time-consuming method.

An object of the present invention is to provide a method and a reagent for the simple and sensitive determination of cholesterol in remnant-like particles without the separation of components of a sample.

SUMMARY OF THE INVENTION

The present inventor has found that in the determination of cholesterol in a biological sample containing lipoproteins such as HDL, LDL, chylomicrons (CM), very low density lipoprotein (VLDL), CM remnant, VLDL remnant and intermediate density lipoprotein (IDL) by using cholesterol esterase and cholesterol oxidase or cholesterol dehydrogenase, cholesterol in remnant-like particles (e.g., CM remnant, VLDL remnant and IDL remnant) can be specifically determined by additionally using phospholipase. The present invention has been completed based on this finding.

That is, the present invention relates to the following (1)–(18).

(1) A method for the quantitative determination of cholesterol in remnant-like particles in a biological sample, which comprises contacting the biological sample with (i) cholesterol esterase, (ii) cholesterol oxidase or cholesterol dehydrogenase, and (iii) phospholipase in an aqueous medium in the presence of oxygen or an oxidized coenzyme, and measuring the formed hydrogen peroxide or reduced coenzyme.

(2) The method according to (1) wherein a surfactant exists in the aqueous medium when the biological sample is contacted with (i) cholesterol esterase, (ii) cholesterol oxidase or cholesterol dehydrogenase, and (iii) phospholipase.

(3) The method according to (1) wherein a surfactant is added to the biological sample prior to the contact with (i) cholesterol esterase, (ii) cholesterol oxidase or cholesterol dehydrogenase, and (iii) phospholipase.

(4) The method according to (2) or (3) wherein said surfactant is a surfactant which inhibits the action of cholesterol esterase and cholesterol oxidase or cholesterol dehydrogenase on cholesterol in lipoproteins other than remnant-like particles.

(5) The method according to any of (2) to (4) wherein said surfactant is a polyoxyalkylene derivative or a polyoxyethylene-polyoxypropylene copolymer or its derivative.

(6) The method according to (1) wherein a polyoxyethylene-polyoxypropylene copolymer or its derivative is added to the biological sample prior to the contact with (i) cholesterol esterase, (ii) cholesterol oxidase or cholesterol dehydrogenase, and (iii) phospholipase, and a polyoxyalkylene derivative is added when the biological sample is contacted with (i) cholesterol esterase, (ii) cholesterol oxidase or cholesterol dehydrogenase, and (iii) phospholipase.

(7) The method according to (5) or (6) wherein said polyoxyalkylene derivative is polyoxyethylene alkyl ether, polyoxyethylenestyrenated phenyl ether or polyoxyethylene long-chain branched alkyl ether.

(8) The method according to (5) or (6) wherein said polyoxyethylene-polyoxypropylene copolymer or its derivative is a compound represented by general formula (I):

$$RO-(C_2H_4O)_a-(C_3H_6O)_b-(C_2H_4O)_c-H \qquad (I)$$

(wherein a, b and c, which may be the same or different, each represents an integer of 1 to 200, and R represents straight-chain or branched alkyl).

(9) The method according to any of (1) to (8) wherein said phospholipase is phospholipase D, phospholipase C or phospholipase A2.

(10) A reagent for the quantitative determination of cholesterol in remnant-like particles, comprising (i) cholesterol esterase, (ii) cholesterol oxidase or cholesterol dehydrogenase, and (iii) phospholipase.

(11) The reagent according to (10), further comprising a surfactant. (12) The reagent according to (11) which comprises a first reagent comprising the surfactant and a second reagent comprising (i) cholesterol esterase, (ii) cholesterol oxidase or cholesterol dehydrogenase, and (iii) phospholipase.

(13) The reagent according to (11) or (12) wherein said surfactant is a surfactant which inhibits the action of cholesterol esterase and cholesterol oxidase or cholesterol dehydrogenase on cholesterol in lipoproteins other than remnant-like particles.

(14) The reagent according to (11) or (12) wherein said surfactant is a polyoxyalkylene derivative or a polyoxyethylene-polyoxypropylene copolymer or its derivative.

(15) The reagent according to (12) wherein said surfactant in the first reagent is a polyoxyethylene-polyoxypropylene copolymer and the second reagent further comprises a polyoxyalkylene derivative.

(16) The reagent according to (14) or (15) wherein said polyoxyalkylene derivative is polyoxyethylene alkyl ether, polyoxyethylenestyrenated phenyl ether or polyoxyethylene long-chain branched alkyl ether.

(17) The reagent according to (14) or (15) wherein said polyoxyethylene-polyoxypropylene copolymer or its derivative is a compound represented by general formula (I):

$$RO-(C_2H_4O)_a-(C_3H_6O)_b-(C_2H_4O)_c-H \qquad (I)$$

(wherein a, b and c, which may be the same or different, each represents an integer of 1 to 200, and R represents straight-chain or branched alkyl).

(18) The reagent according to any of (10) to (17) wherein said phospholipase is phospholipase D, phospholipase C or phospholipase A2.

DETAILED DESCRIPTION OF THE INVENTION

Figure 1:
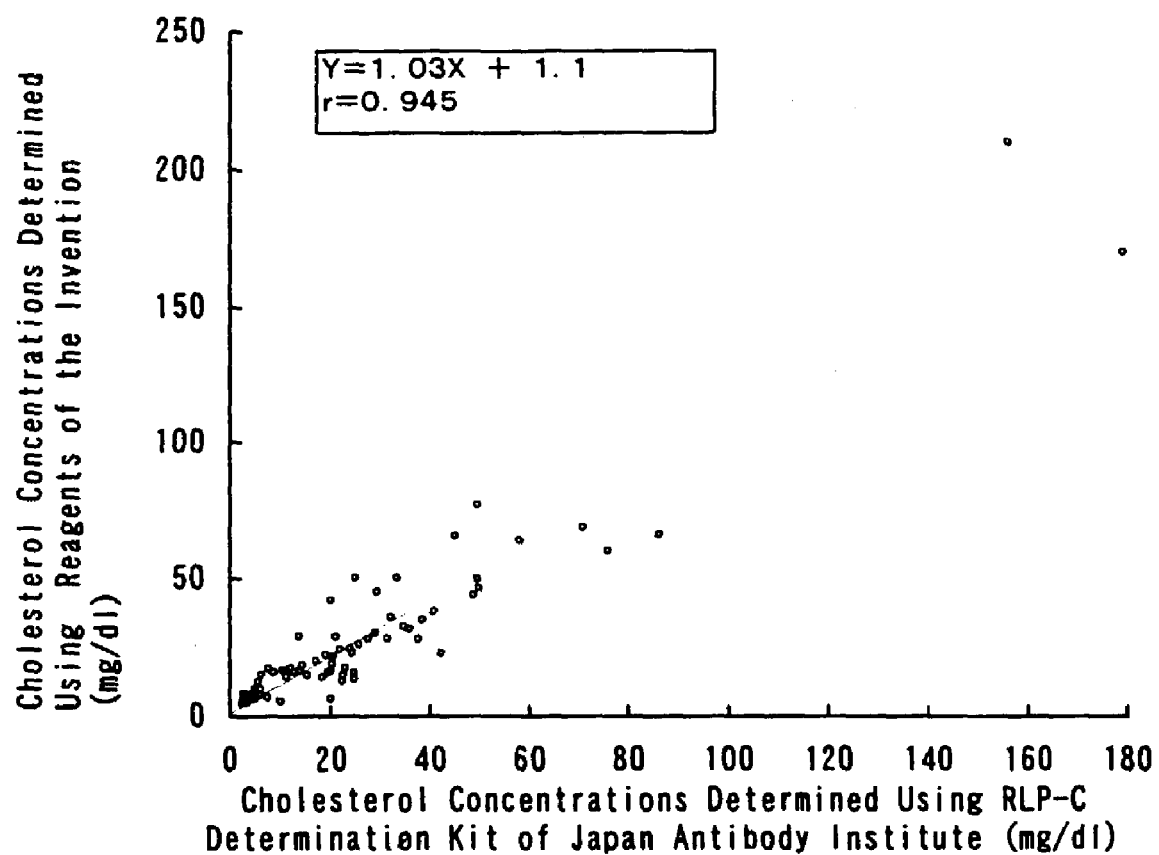
FIG. 1 is a graph showing the correlation between the cholesterol concentrations (mg/dl) determined using the reagents of Example 1 (ordinate) and those determined using the RLP-C determination kit of Japan Antibody Institute (abscissa).

The reaction for the determination of cholesterol in remnant-like particles according to the present invention is carried out in an aqueous medium, preferably in a buffer solution. Buffers useful in the buffer solution include tris (hydroxymethyl)aminomethane, phosphate buffer, borate buffer and Good's buffer. Examples of Good's buffer are N-(2-acetamido)-2-aminoethanesulfonic acid (ACES), N-(2-acetamido)iminodiacetic acid (ADA), N,N-bis(2-hydroxyethyl)-2-aminoethanesulfonic acid (BES), 3-[N,N-bis (2-hydroxyethyl)amino]-2-hydroxypropanesulfonic acid (DIPSO), N-(2-hydroxyethyl)piperazine-N'-2-ethanesulfonic acid (HEPES), 2-(N-morpholino)ethanesulfonic acid (MES), 3-(N-morpholino)propanesulfonic acid (MOPS), 3-(N-morpholino)-2-hydroxypropanesulfonic acid (MOPSO), piperazine-N,N'-bis(2-ethanesulfonic acid) (PIPES) and piperazine-N,N'-bis(2-hydroxypropane-3-sulfonic acid) (POPSO).

The pH of the buffer solution is 4 to 10, preferably 5 to 9. The concentration of the buffer is preferably 5 to 500 mM, more preferably 10 to 200 mM, particularly preferably 20 to 100 mM.

As the cholesterol esterase, any enzyme capable of hydrolyzing cholesterol ester can be used. Suitable enzymes include cholesterol esterases and lipoprotein lipases derived from microorganisms and animals.

As the cholesterol oxidase, any enzyme capable of oxidizing cholesterol to form hydrogen peroxide can be used. Suitable enzymes include cholesterol oxidases derived from microorganisms and animals.

As the cholesterol dehydrogenase, any enzyme capable of oxidizing cholesterol and reducing an oxidized coenzyme can be used. Suitable enzymes include cholesterol dehydrogenases derived from microorganisms and animals.

In order to improve the specificity and stability of these enzymes, they may be chemically modified with a group having polyethylene glycol as a main component, a water-soluble oligosaccharide residue, a sulfopropyl group, or the like. Enzymes obtained by recombinant DNA techniques can also be used.

The respective concentration of cholesterol esterase, cholesterol oxidase and cholesterol dehydrogenase in a reaction mixture is preferably 0.01 to 200 U/ml, more preferably 0.1 to 100 U/ml.

In the reaction for the determination of cholesterol in remnant-like particles according to the present invention, surfactants or cholic acids which are often used to activate cholesterol esterase, cholesterol oxidase and cholesterol dehydrogenase can additionally be used so far as they do not affect the specificity of the reaction. Further, various salts for solubilizing proteins such as globulin in a biological sample may be used.

Surfactants useful for activating cholesterol esterase, cholesterol oxidase and cholesterol dehydrogenase include anionic surfactants such as alkyl sulfonate (e.g., 1-pentasulfonate, 1-hexasulfonate, 1-heptasulfonate and 1-octasulfonate). The surfactants are used at a concentration of 0 to 5%. As the cholic acid, cholic acid, deoxycholic acid, taurocholic acid, chenodeoxycholic acid, etc. can be used at a concentration of 0 to 5%.

Examples of the salts are sodium chloride, sodium sulfate, potassium chloride, potassium sulfate, magnesium chloride, magnesium sulfate, magnesium acetate, lithium chloride, lithium sulfate, ammonium chloride, ammonium sulfate, magnesium nitrate and calcium nitrate. The salts are used at a concentration of 0 to 100 mM.

As the phospholipase, any enzyme capable of hydrolyzing phospholipids can be used. Suitable enzymes include phospholipases derived from animals, plants and microorganisms, for example, phospholipase D, phospholipase C and phospholipase A2.

The concentration of phospholipase in a reaction mixture is preferably 0.01 to 200 U/ml, more preferably 0.1 to 100 U/ml.

When a combination of cholesterol esterase and cholesterol oxidase is used, the reaction catalyzed by these enzymes results in the formation of hydrogen peroxide from oxygen. The determination of the formed hydrogen peroxide can be carried out, for example, by forming a pigment using 4-aminoantipyrine and phenol, 4-aminoantipyrine and Trinder's reagent, or a highly sensitive chromogen, in the presence of peroxidase, and by measuring the absorbance of a reaction mixture colored by the formed pigment.

Examples of suitable phenols are phenol, 4-chlorophenol, m-cresol and 3-hydroxy-2,4,6-triiodobenzoic acid (HTIB).

Examples of the Trinder's reagents (General Catalog of Dojin Kagaku Kenkyusho, 19th ed., 1994) are anilines such as N-sulfopropylaniline, N-ethyl-N-(2-hydroxy-3-sulfopropyl)-m-toluidine (TOOS), N-ethyl-N-(2-hydroxy-3-sulfopropyl)-3,5-dimethylaniline (MAOS), N-ethyl-N-(2-hydroxy-3-sulfopropyl)-3,5-dimethoxyaniline (DAOS), N-ethyl-N-sulfopropyl-m-toluidine (TOPS), N-(2-hydroxy-3-sulfopropyl)-3,5-dimethoxyaniline (HDAOS), N,N-dimethyl-m-toluidine, N,N-disulfopropyl-3,5-dimethoxyaniline, N-ethyl-N-sulfopropyl-m-anisidine, N-ethyl-N-sulfopropylaniline, N-ethyl-N-sulfopropyl-3,5-dimethoxyaniline, N-sulfopropyl-3,5-dimethoxyaniline, N-ethyl-N-sulfopropyl-3,5-dimethylaniline, N-ethyl-N-(2-hydroxy-3-sulfopropyl)-m-anisidine, N-ethyl-N-(2-hydroxy-3-sulfopropyl) aniline and N-ethyl-N-(2-hydroxy-3-sulfopropyl)-3,5-dimethoxyaniline, N-ethyl-N-(3-methylphenyl)-N'-succinylethylenediamine (EMSE), and N-ethyl-N-(3-methylphenyl)-N'-acetylethylenediamine.

Examples of the highly sensitive chromogens are 10-(N-methylcarbamoyl)-3,7-bis(dimethylamino)phenothiadine (MCDP) disclosed in Japanese Published Examined Patent Application No. 33479/85, bis[3-bis(4-chlorophenyl)methyl-4-dimethylaminophenyl] amine (BCMA) disclosed in Japanese Published Examined Patent Application No. 27839/92, and the compound disclosed in Japanese Published Unexamined Patent Application No. 296/87.

The concentration of these phenols, 4-aminoantipyrine, Trinder's reagents and highly sensitive chromogens is preferably 0.01 to 10 mg/ml.

When a combination of cholesterol esterase and cholesterol dehydrogenase is used, the reaction catalyzed by these enzymes results in the formation of NAD(P)H, which is a reduced coenzyme, from NAD(P), which is an oxidized coenzyme. The formed NAD(P)H can be determined by measuring the absorbance of a reaction mixture at 300 to 500 nm, preferably 330 to 400 nm, particularly preferably ca. 340 nm. The determination of NAD(P)H can also be carried out by forming a formazan pigment by addition of diaphorase and a tetrazolium salt and then determining the formazan pigment by colorimetry.

The enzymatic reactions are carried out at 10 to 50° C., preferably 30 to 40° C., usually 37° C., for 1 to 30 minutes, preferably 2 to 10 minutes.

There is no specific restriction as to the biological sample to which the present invention is applied. For example, the invention is applicable to blood and blood fractions such as plasma and serum.

In the present invention, in order to improve the accuracy of the determination of cholesterol in remnant-like particles, it is preferred to add a surfactant which inhibits the action of cholesterol esterase and cholesterol oxidase or cholesterol dehydrogenase on cholesterol in lipoproteins other than remnant-like particles, alone or in combination with the above-mentioned surfactant which activates cholesterol esterase and cholesterol oxidase or cholesterol dehydrogenase. This surfactant may be added when the biological sample is contacted with (i) cholesterol esterase, (ii) cholesterol oxidase or cholesterol dehydrogenase, and (iii) phospholipase, together with these enzymes, but is preferably added to the biological sample prior to the contact with these enzymes.

As the surfactant which inhibits the action of cholesterol esterase and cholesterol oxidase or cholesterol dehydrogenase on cholesterol in lipoproteins other than remnant-like particles, any surfactant can be used that reduces the action of cholesterol esterase and cholesterol oxidase or cholesterol dehydrogenase on cholesterol in lipoproteins other than remnant-like particles. Useful surfactants include polyoxyalkylene derivatives and polyoxyethylene-polyoxypropylene copolymers or derivatives thereof.

Suitable polyoxyalkylene derivatives include polyoxyethylene alkyl ether, polyoxyethylenestyrenated phenyl ether and polyoxyethylene long-chain branched alkyl ether. The alkyl in these derivatives includes alkyl having 8 or more carbon atoms such as octyl and nonyl.

Examples of the polyoxyalkylene derivatives include commercially available polyoxyethylene alkyl ethers such as Nonion HS-210, Nonion HS-215, Nonion HS-208.5 and Nonion HS-208 (all produced by NOF Corporation) and Emulgen L-40, Emulgen 911 and Emulgen 810 (all produced by Kao Corporation), commercially available polyoxyethylenestyrenated phenyl ethers such as BLAUNON TSP-50 (Aoki Yushi Co., Ltd.), and commercially available polyoxyethylene long-chain branched alkyl ethers such as Unilube MT0620B (NOF Corporation).

The hydrophile-lipophile balance (hereinafter referred to as HLB) of the polyoxyalkylene derivatives is preferably 9 to 20.

The polyoxyethylene-polyoxypropylene copolymers include random copolymers and block copolymers of polyoxyethylene and polyoxypropylene. An example of the copolymer is a compound represented by general formula (I):

$$RO-(C_2H_4O)_a-(C_3H_6O)_b-(C_2H_4O)_c-H \qquad (I)$$

(wherein a, b and c, which may be the same or different, each represents an integer of 1 to 200, and R represents straight-chain or branched alkyl).

The straight-chain or branched alkyl is preferably alkyl having 1 to 30 carbon atoms, more preferably alkyl having 2 to 24 carbon atoms.

Examples of the compounds represented by general formula (I) include commercially available ones such as Pullulonic L-121, Pullulonic L-122, Pullulonic L-101, Pullulonic P-103 and Pullulonic F-108 (all produced by Asahi Denka Kogyo Co. Ltd.). The molecular weight of the polypropylene glycol group in the compounds represented by general formula (I) is preferably 2050 or more, more preferably 2750 or more, particularly preferably 3250 or more. The HLB of the polyoxyethylene-polyoxypropylene copolymers is preferably 1 to 6.

The concentration of the surfactant which inhibits the action of cholesterol esterase and cholesterol oxidase or cholesterol dehydrogenase on cholesterol in lipoproteins other than remnant-like particles is not specifically limited, but is preferably 0.001 to 10%, more preferably 0.01 to 5%, particularly preferably 0.05 to 1%.

The reaction mixture may further comprise a lipoprotein coagulant, an additional enzyme, etc., if necessary.

Examples of the lipoprotein coagulant are polyanions such as phosphorus wolframate, dextran sulfate and heparin, and salts of divalent metals such as magnesium, calcium and cobalt. An example of the additional enzyme is ascorbate oxidase.

Certain embodiments of the present invention are illustrated in the following examples.

EXAMPLE 1

The following reagents for the determination of cholesterol in remnant-like particles were prepared.

| Reagent 1 | |
|---|---|
| Good's buffer pH 6.8 (MOPS, Dojin Kagaku Co., Ltd.) | 20 mM |
| TOOS (Dojin Kagaku Co., Ltd.) | 0.3 g/l |
| Sodium sulfate | 2 g/l |
| Pullulonic F-108 (Asahi Denka Kogyo Co., Ltd.) | 1 g/l |
| Peroxidase (POD, Toyobo Co., Ltd.) | 10 U/ml |
| Ascorbate oxidase (AOD, Asahi Chemical Industry Co., Ltd.) | 2 U/ml |
| Reagent 2 | |
| Good's buffer pH 6.8 (MOPS, Dojin Kagaku Co., Ltd.) | 20 mM |
| 4-Aminoantipyrine (Nacalai Kagaku Co., Ltd.) | 0.5 g/l |
| Emulgen L-40 (Kao Corporation) | 2 g/l |
| Peroxidase (Toyobo Co., Ltd.) | 10 U/ml |
| Cholesterol esterase (CEBP, Asahi Chemical Industry Co., Ltd.) | 1 U/ml |
| Cholesterol oxidase (Kyowa Hakko Kogyo Co., Ltd.) | 2 U/ml |
| Phospholipase D (Asahi Chemical Industry Co., Ltd.) | 5 U/ml |

EXAMPLE 2

The following reagents for the determination of cholesterol in remnant-like particles were prepared.

| Reagent 1 | |
|---|---|
| Good's buffer pH 6.8 (MOPS, Dojin Kagaku Co., Ltd.) | 20 mM |
| TOOS (Dojin Kagaku Co., Ltd.) | 0.3 g/l |
| Sodium sulfate | 2 g/l |
| BLAUNON TSP-50 (Aoki Yushi Co., Ltd.) | 2 g/l |
| Peroxidase (POD, Toyobo Co., Ltd.) | 10 U/ml |
| Ascorbate oxidase (AOD, Asahi Chemical Industry Co., Ltd.) | 2 U/ml |
| Reagent 2 | |
| Good's buffer pH 6.8 (MOPS, Dojin Kagaku Co., Ltd.) | 20 mM |
| 4-Aminoantipyrine (Nacalai Kagaku Co., Ltd.) | 0.5 g/l |
| Emulgen L-40 (Kao Corporation) | 2 g/l |
| Peroxidase (Toyobo Co., Ltd.) | 10 U/ml |
| Cholesterol esterase (CEBP, Asahi Chemical Industry Co., Ltd.) | 1 U/ml |
| Cholesterol oxidase (Kyowa Hakko Kogyo Co., Ltd.) | 2 U/ml |
| Phospholipase D (Asahi Chemical Industry Co., Ltd.) | 5 U/ml |

EXAMPLE 3

The following reagents for the determination of cholesterol in remnant-like particles were prepared.

| Reagent 1 | |
|---|---|
| Good's buffer pH 6.8 (MOPS, Dojin Kagaku Co., Ltd.) | 20 mM |
| TOOS (Dojin Kagaku Co., Ltd.) | 0.3 g/l |
| Sodium sulfate | 2 g/l |
| Unilube MT-0620B (NOF Corporation) | 0.5 g/l |
| Peroxidase (POD, Toyobo Co., Ltd.) | 10 U/ml |
| Ascorbate oxidase (AOD, Asahi Chemical Industry Co., Ltd.) | 2 U/ml |
| Reagent 2 | |
| Good's buffer pH 6.8 (MOPS, Dojin Kagaku Co., Ltd.) | 20 mM |
| 4-Aminoantipyrine (Nacalai Kagaku Co., Ltd.) | 0.5 g/l |
| Emulgen L-40 (Kao Corporation) | 2 g/l |
| Peroxidase (Toyobo Co., Ltd.) | 10 U/ml |
| Cholesterol esterase (CEBP, Asahi Chemical Industry Co., Ltd.) | 1 U/ml |
| Cholesterol oxidase (Kyowa Hakko Kogyo Co., Ltd.) | 2 U/ml |
| Phospholipase D (Asahi Chemical Industry Co., Ltd.) | 5 U/ml |

EXAMPLE 4

The following reagents for the determination of cholesterol in remnant-like particles were prepared.

| Reagent 1 | |
|---|---|
| Good's buffer pH 6.8 (MOPS, Dojin Kagaku Co., Ltd.) | 20 mN |
| TOOS (Dojin Kagaku Co., Ltd.) | 0.3 g/l |
| Sodium sulfate | 2 gIl |
| BLAUNON TSP-50 (Aoki Yushi Co., Ltd.) | 2 g/l |
| Peroxidase (POD, Toyobo Co., Ltd.) | 10 U/ml |
| Ascorbate oxidase (AOD, Asahi Chemical Industry Co., Ltd.) | 2 U/ml |
| Reagent 2 | |
| Good's buffer pH 6.8 (MOPS, Dojin Kagaku Co., Ltd.) | 20 mM |
| 4-Aminoantipyrine (Nacalai Kagaku Co., Ltd.) | 0.5 g/l |
| Emulgen L-40 (Kao Corporation) | 2 g/l |
| Peroxidase (Toyobo Co., Ltd.) | 10 U/ml |
| Cholesterol esterase (CEBP, Asahi Chemical Industry Co., Ltd.) | 1 U/ml |
| Cholesterol oxidase (Kyowa Hakko Kogyo Co., Ltd.) | 2 U/ml |
| Phospholipase C (Asahi Chemical Industry Co., Ltd) | 20 U/ml |

EXAMPLE 5

The following reagents for the determination of cholesterol in remnant-like particles were prepared.

| Reagent 1 | |
|---|---|
| Good's buffer pH 6.8 (MOPS, Dojin Kagaku Co., Ltd.) | 20 mM |
| TOOS (Dojin Kagaku Co., Ltd.) | 0.3 g/l |
| Sodium sulfate | 2 g/l |
| BLAUNON TSP-50 (Aoki Yushi Co., Ltd.) | 2 g/l |
| Peroxidase (POD, Toyobo Co., Ltd.) | 10 U/ml |
| Ascorbate oxidase (AOD, Asahi Chemical Industry Co., Ltd.) | 2 U/ml |
| Reagent 2 | |
| Good's buffer pH 6.8 (MOPS, Dojin Kagaku Co., Ltd.) | 20 mM |
| 4-Aminoantipyrine (Nacalai Kagaku Co., Ltd.) | 0.5 g/l |
| Emulgen L-40 (Kao Corporation) | 2 g/l |
| Peroxidase (Toyobo Co., Ltd.) | 10 U/ml |
| Cholesterol esterase (CEBP, Asahi Chemical Industry Co., Ltd.) | 1 U/ml |
| Cholesterol oxidase (Kyowa Hakko Kogyo Co., Ltd.) | 2 U/ml |
| Phospholipase A2 (Asahi Chemical Industry Co., Ltd.) | 50 U/ml |

EXAMPLE 6

Seventy fresh serum samples were subjected to the determination of cholesterol in remnant-like particles according to the following procedure.

Reagent 1 of Example 1 (2.25 ml) was put into a cell of a spectrophotometer and 30 µl of a serum was added thereto, followed by stirring and then heating at 37° C. for 5 minutes. To the cell was added 0.75 ml of Reagent 2 of Example 1 previously heated to 37° C., followed by stirring and then heating for 5 minutes. The change in absorbance at 555 nm was measured. The same procedure was repeated using a standard serum solution having a concentration of cholesterol in remnant-like particles of 49.6 mg/dl as determined by the RLP-C determination kit of Japan Antibody Institute to prepare a calibration curve. The concentration of cholesterol in remnant-like particles in the sample was determined from the above change in absorbance.

Separately, the above 70 fresh serum samples were subjected to the determination of cholesterol in remnant-like particles using the RLP-C determination kit of Japan Antibody Institute. The correlation between the obtained values and the values obtained above was examined.

The result is shown in FIG. 1. The cholesterol concentrations (mg/dl) determined using the reagents of Example 1 and those determined using the RLP-C determination kit of Japan Antibody Institute, which is a reagent for the determination of cholesterol in remnant-like particles, showed a good correlation, giving a coefficient of correlation of 0.945. This result indicates that cholesterol in remnant-like particles can be determined by a simple procedure by the use of the reagents of Example 1.

EXAMPLE 7

The experiment was carried out in the same manner as in Example 6, except for the use of the reagents of Example 2. The obtained coefficient of correlation was 0.84. This result indicates that cholesterol in remnant-like particles can be determined by a simple procedure by the use of the reagents of Example 2.

EXAMPLE 8

The experiment was carried out in the same manner as in Example 6, except for the use of the reagents of Example 3. The obtained coefficient of correlation was 0.93. This result indicates that cholesterol in remnant-like particles can be determined by a simple procedure by the use of the reagents of Example 3.

EXAMPLE 9

The experiment was carried out in the same manner as in Example 6, except for the use of the reagents of Example 4. The obtained coefficient of correlation was 0.87. This result indicates that cholesterol in remnant-like particles can be determined by a simple procedure by the use of the reagents of Example 4.

EXAMPLE 10

The experiment was carried out in the same manner as in Example 6, except for the use of the reagents of Example 5. The obtained coefficient of correlation was 0.85. This result indicates that cholesterol in remnant-like particles can be determined by a simple procedure by the use of the reagents of Example 5.

What is claimed is:

1. A method for quantitatively determining cholesterol in renmant-like particles in a biological sample, which comprises:
    (I) contacting the biological sample with (i) cholesterol esterase, (ii) cholesterol oxidase or cholesterol dehydrogenase, and (iii) phospholipase and (iv) a surfactant which inhibits action of cholesterol esterase and cholesterol oxidase or cholesterol dehydrogenase on cholesterol in lipoproteins other than remnant-like particles, in an aqueous medium in the presence of oxygen or an oxidized coenzyme,
    (II) measuring formed hydrogen peroxide or reduced coenzyme, and
    (III) correlating the measured hydrogen peroxide or reduced coenzyme to a quantitative determination of said cholesterol in remnant-like particles.

2. The method according to claim 1 wherein said surfactant is a polyoxyalkylene derivative or a polyoxyethylene-polyoxypropylene copolymer or its derivative.

3. The method according to claim 1 wherein a polyoxyethylene-polyoxypropylene copolymer or its derivative is added to the biological sample prior to the contact (I) with (i) cholesterol esterase, (ii) cholesterol oxidase or cholesterol dehydrogenase, and (iii) phospholipase, and wherein a polyoxyalkylene derivative is added when the biological sample is contacted (I) with (i) cholesterol esterase, (ii) cholesterol oxidase or cholesterol dehydrogenase, and (iii) phospholipase.

4. The method according to claim 2 or 3 wherein said polyoxyalkylene derivative is polyoxyethylene alkyl ether, polyoxyethylenestyrenated phenyl ether or polyoxyethylene long-chain branched alkyl ether.

5. The method according to claim 4 wherein said phospholipase is phospholipase D, phospholipase C or phospholipase A2.

6. The method according to claim 2 or 3 wherein said polyoxyethylene-polyoxypropylene copolymer or its derivative is a compound represented by $$RO-(C_2H_4O)_a-(C_3H_6O)_b-(C_2H_4O)_c-H \qquad (I)$$

wherein a, b and c independently represent an integer of 1 to 200, and R represents hydrogen, or a straight-chain or branched alkyl.

7. The method according to claim 6, wherein R is straight-chain or branched alkyl.

8. The method according to claim 6 wherein R is hydrogen.

9. The method according to claim 6 wherein said phospholipase is phospholipase D, phospholipase C or phospholipase A2.

10. The method according to claim 9, wherein R is straight-chain or branched alkyl.

11. The method according to claim 9, wherein R is hydrogen.

12. The method according to any of claims 1–3 wherein said phospholipase is phospholipase D, phospholipase C or phospholipase A2.

* * * * *

UNITED STATES PATENT AND TRADEMARK OFFICE
CERTIFICATE OF CORRECTION

| | |
|---|---|
| PATENT NO. | : 7,202,047 B2 |
| APPLICATION NO. | : 10/430231 |
| DATED | : April 10, 2007 |
| INVENTOR(S) | : Kazuhito Miyauchi |

It is certified that error appears in the above-identified patent and that said Letters Patent is hereby corrected as shown below:

ON TITLE PAGE AT (56) OTHER PUBLICATIONS

After "Uematsu, et al.": "Biochmica" should read --Biochimica--.

COLUMN 2

Line 46, "(12)" should read --¶ (12)--.

COLUMN 3

Line 27, "Buffers" should read --¶ Buffers--.

COLUMN 10

Line 33, "(I)" should be deleted.

Signed and Sealed this

Tenth Day of July, 2007

JON W. DUDAS
*Director of the United States Patent and Trademark Office*